(12) United States Patent
Kohara

(10) Patent No.: US 7,645,813 B2
(45) Date of Patent: Jan. 12, 2010

(54) PRESSURE-SENSITIVE ADHESIVE FOR THE SKIN AND TAPES OR SHEETS FOR THE SKIN MADE BY USING THE SAME

(75) Inventor: Minoru Kohara, Kyoto (JP)

(73) Assignee: CosMED Pharmaceutical Co., Ltd., Kyoto (JP)

( * ) Notice: Subject to any disclaimer, the term of this patent is extended or adjusted under 35 U.S.C. 154(b) by 602 days.

(21) Appl. No.: 10/486,115

(22) PCT Filed: Aug. 8, 2002

(86) PCT No.: PCT/JP02/08153

§ 371 (c)(1),
(2), (4) Date: Feb. 9, 2004

(87) PCT Pub. No.: WO03/014247

PCT Pub. Date: Feb. 20, 2003

(65) Prior Publication Data

US 2004/0234582 A1 Nov. 25, 2004

(30) Foreign Application Priority Data

Aug. 10, 2001 (JP) .............................. 2001-278905

(51) Int. Cl.
*C08L 15/00* (2006.01)
(52) U.S. Cl. ........................ 523/111; 424/400; 424/443; 427/31; 514/772; 514/772.1; 514/772.3; 514/772.4
(58) Field of Classification Search ................... 424/449
See application file for complete search history.

(56) References Cited

U.S. PATENT DOCUMENTS

| 5,968,547 A | * | 10/1999 | Reder et al. | .................. | 424/449 |
| 6,203,913 B1 | * | 3/2001 | Kondos et al. | ........... | 428/423.1 |
| 6,608,143 B1 | * | 8/2003 | Fukuoka et al. | ............. | 525/309 |
| 6,632,906 B1 | * | 10/2003 | Kamiyama | .................. | 526/316 |
| 6,682,757 B1 | * | 1/2004 | Wright | ........................ | 424/448 |
| 6,870,006 B2 | * | 3/2005 | Cavalli et al. | ................ | 525/123 |

FOREIGN PATENT DOCUMENTS

| JP | 07-2928 A | 1/1965 |
| JP | 2700835 B2 | 9/1991 |
| JP | 05-194631 | 8/1993 |
| JP | 05-247119 A | 9/1993 |
| JP | 06-32847 A | 2/1994 |
| JP | 3014188 B2 | 2/1994 |
| JP | 10-251609 | 9/1998 |
| JP | 11-269439 A | 10/1999 |
| JP | 11-286664 A | 10/1999 |
| JP | 2000-001653 | 1/2000 |
| JP | 2001-164211 | 6/2001 |
| JP | 2001-288438 | 10/2001 |
| JP | 2002-121522 | 4/2002 |
| WO | WO9959808 | * 11/1999 |

* cited by examiner

Primary Examiner—Eric E Silverman
(74) Attorney, Agent, or Firm—Townsend & Banta

(57) ABSTRACT

The invention provides a pressure-sensitive adhesive for the skin excellent in pressure-sensitive adhesiveness to the human skin and repeelability therefrom, which does not cause the horny layer to be torn away in peeling and is lowly irritant to the skin; and tapes or sheets made by using the same. The pressure-sensitive adhesive is characterized by comprising (a) 100 parts by weight of a copolymer which is prepared from an olefinic macromonomer and a vinyl monomer and whose molecular weight (in terms of polystyrene and as determined by gel permeation chromatography (GPC)) has a two-peak distribution (with the proviso that when the copolymer is to be post-cured, the distribution is one as determined before the post cure) and (b) 20 to 250 parts by weight of a softener which is compatible with the copolymer and liquid or pasty at room temperature and has a boiling point of 250 or above (with the proviso that when the content of the softener (b) exceeds 80 parts by weight, the copolymer must be post-cured).

7 Claims, No Drawings

PRESSURE-SENSITIVE ADHESIVE FOR THE SKIN AND TAPES OR SHEETS FOR THE SKIN MADE BY USING THE SAME

TECHNICAL FIELD

This invention relates to a tape or sheet for the skins, particularly relates to a tape or sheet which has good adhesiveness, re-peelability, and low skin irritation to the skin.

BACKGROUND ART

In the field of medical pressure sensitive adhesive tape, the needs over the products which are gentle to the skin, and are free from damage of skin after repeated application to the skin. In this regard, there are some example tapes that are so-called low adhesion type tape made from acrylics and rubber. However, these products also cause some problems. After applying the tape to the skin, the adhesion increases with time, and the peeling of tape off the skin becomes difficult and a part of adhesive leaves on the skin after removal.

For example, the re-peelable medical adhesives which consist of acrylic-acid and acrylic-ester copolymer are described in, JP 2700835, JP 3014188, Laid-open Publication H 11-269439 and Laid-open Publication H 11-286664. The crosslinking of acrylic acid in the adhesive copolymer by isocyanate is described in the later 2 patents. However, the isocyanate is quite reactive for many compounds and often reacts with the drugs in the adhesive. In this case, the crosslinking reaction itself is inhibited.

In Laid-open Publication H 10-251609, described is the re-peelable type adhesive which consists of acrylic AB type block copolymer. However, The manufacturing of acrylic AB block adhesive has many technological problems and it is difficult to supply it at the present situation.

SUMMARY OF THE INVENTION

The present invention is invented in view of the problems described above, and its object is to provide a pressure-sensitive adhesive for the skin excellent in pressure-sensitive adhesiveness to the human skin and repeelability therefrom, which does not cause the horny layer to be torn away in peeling and is lowly irritant to the skin; and tapes or sheets made by using the same.

The inventive pressure-sensitive adhesive for the skin is characterized by comprising (a) 100 parts by weight of a copolymer which is prepared from an olefinic macromonomer and a vinyl monomer and whose molecular weight (in terms of polystyrene and as determined by gel permeation chromatography (GPC)) has a two-peak distribution (with the proviso that when the copolymer is to be post-cured, the distribution is one as determined before the post cure) and (b) 20 to 250 parts by weight of a softener which is compatible with the copolymer and liquid or pasty at room temperature and has a boiling point of 250 or above (with the proviso that when the content of the softener (b) exceeds 80 parts by weight, the copolymer must be post-cured).

The inventive pressure adhesive tape or sheet for the skin is characterized in that the above pressure sensitive adhesive is disposed on at least of one surface of a substrate. In accordance with a particular aspect of the present invention, skin permeable active ingredient is added to the adhesive.

DISCLOSURE OF THE INVENTION

The pressure sensitive adhesive for the skin of this invention comprises;

(a) 100 parts by weight of a copolymer which is prepared from an olefinic macromonomer and a vinyl monomer and whose molecular weight (in terms of polystyrene and as determined by gel permeation chromatography (GPC)) has a two-peak distribution (with the proviso that when the copolymer is to be post-cured, the distribution is one as determined before the post cure) and (b) 20 to 250 parts by weight of a softener which is compatible with the copolymer and liquid or pasty at room temperature and has a boiling point of 250 or above (with the proviso that when the content of the softener (b) exceeds 80 parts by weight, the copolymer must be post-cured).

The olefinic macromonomer in this invention means the olefinic polymer which has end unsaturated structure and has ability of radical polymerization. In other words, it is a polyolefin with a double bond at one terminal, having a nature of polymerization with other monomers. The said polyolefin may be, polyethylene, polypropylene, ethylene-propylene copolymer, and ethylene-butylene copolymer. As double bond group which has radical polymerization ability, vinyl group, acryloyl group, and allyl group are listed as examples.

The example of said olefinic macromonomer is an ethylene-butylene copolymer end terminated with methyl methacrylate, brand name "KRATON LIQUID Polymer HPVM-1253" (made by Shell Chemical Company). Also, in Laid-open Publication H5 194631, in Laid-open Publication H5 247119, in Laid-open Publication H6 32847, and in Laid-open Publication H7 2928, described is polypropylene or ethylene-propylene random copolymer with (meth)acrylic acid alkylester terminal, such as methyl methacrylate.

The content of said olefinic macromonomer in said copolymer is 20-65 weight %. When the content is lower, the concentration of softener dissolved in copolymer decreases; while the content is higher, the copolymer becomes gel at the time of polymerization, or the viscosity of copolymer becomes higher and would be difficult for handling.

The preferred examples of vinyl monomer for said copolymer are alkyl (meth)acrylate having 4-18 carbon atoms in the alkyl group, such as butyl, pentyl, hexyl, heptyl, nonyl, decyl, dodecyl, and 2-ethylhexyl group. The other examples are, (meth)acrylamide, N-vinyl-2-pyrrolidone, vinyl acetate, vinyl propionate, and alkoxyalkyl (meth)acrylate such as methoxyethyl (meth)acrylate, and ethoxyethyl (meth)acrylate, and the like. These monomers may be used independently and may be used together. The preferred content of alkyl (meth)acrylate is 20-40 weight% in said copolymer. When the content is higher, the cohesion of copolymer becomes weaker; and when the content is lower, the adhesion of copolymer becomes weaker.

Preferred copolymer is the one which is composed of one or more monomers selected from the group comprising, alkyl (metha)acrylate, N-vinyl-2-pyrrolidone, vinyl acetate, and methoxyalkyl acrylate. The preferred content of above monomer(s) is 10-40 weight %. When the content is higher, the adhesion of said copolymer decreases; while the content is lower, the solubility of drug in said copolymer decreases.

For the purpose of enabling post-crosslinking of said copolymer, the vinyl monomers which has a functional group may be used together with the above-mentioned vinyl monomers. As the vinyl monomer which has functional group, for example, the acrylic monomer which has hydroxyl group, carboxyl group, glycidyl group, and amino group, or the like, are used. If the content of the vinyl monomer which has the above-mentioned functional group decreases, the crosslinking ability of copolymer decreases; while the content increases, the adhesion of copolymer decreases. So that, the content in copolymer is preferably 0.5-25 weight %, more preferably 0.8-20%.

In the adhesive of this invention, a crosslinking agent may be added for the purpose of increasing the holding power of said copolymer and the softener. The examples of crosslinking agent are, metal chelate compound such as aluminum acetylacetonate, metal Alcoh-late such as tetrabutyl titanate, acid chloride such as adipodichloride, polyamine such as diaminohexane, polyisocyanate, melamine resin, and the like.

If the above-mentioned crosslinking agent content decreases, the crosslinking reaction does not proceed fully; while the content increases, the adhesion of composite decreases. So that 0.01-2.0 weight parts is added to said copolymer of 100 weight parts.

In this invention, however, it is needed for the MWD of said copolymer weight (in terms of polystyrene and as determined by GPC) of said copolymer has a two-peak distribution, (with the proviso that when the copolymer is to be post-cured, the distribution is one as determined before the post cure). If the MWD of polymer does not have two peaks, it becomes impossible to realize the re-peelability and low skin irritation, because the balance of adhesive strength and cohesive force collapses.

Regarding the two peaks of MWD of said copolymer, 200,000-800,000 is the desirable high molecular weight peak, and 2,000-7,000 is the desirable low molecular weight peak. The realization of the re-peelability to the skin and low irritation becomes difficult when the peaks go out of the above range.

Regarding the manufacturing method of said copolymer, for example, the mixture of monomers is dissolved in solvents, such as toluene, ethyl acetate, tetrahydrofuran, and methyl ethyl ketone, together with a polymerization initiator. It is heated under nitrogen atmosphere. As the above-mentioned polymerization initiator, peroxides such as benzoyl peroxide, azo compound such as azobisisobutyronitrile, and the like, are used. The weight average molecular weight of copolymer(A) is ca. 200,000 to 2,000,000.

The softener used in this invention is to give the properties of good adhesiveness, good re-peelability, and low skin irritation, to said copolymer. The softening agent in this invention has properties of (1) liquid or pasty at room temperature, (2) good compatibility to said copolymer, (3) boiling temperature of above 250° C. The examples are, hydrocarbon such as liquid paraffin, squalane, lanolin; and ester such as isopropyl myristate, ethyl laurate, isopropyl adipate, octyl palmitate, isopropyl palmitate, ethyl oleate, octyldodecyl myristate, cetyl isooctanoate, octyldodecyl oleate, glyceryl tri-2-ethylhexanate, neopentyl glycol diethylhexanoate, octyldodecyl lactate, and diisostearyl malate.

These may be used independently, and may be used together and more than one softening agents selected from the group which consists of isopropyl myristate, isopropyl palmitate, ethyl oleate, octyldodecyl myristate, cetyl isooctanoate, octyldodecyl oleate, glyceryl tri-2-ethylhexanate, neopentyl glycol diethylhexanoate, octyldodecyl lactate, and diisostearyl malate.

The amount of addition of said softening agent is 20-250 weight parts to said copolymer of 100 weight parts, and preferably 30-150 weight parts. When the amount of addition decreases, the adhesive strength becomes stronger and the skin irritation increases; while the amount increases, and cohesive force declines. The cohesive force is too low to be useful when the amount of addition of said softening agent exceeds 80 weight parts. In this case, it is necessary to make said copolymer crosslink using the above-mentioned crosslinking agent.

In this invention, tackifier can be added to copolymer composite for the purpose of adjustment of adhesive power or cohesive force, and the amount of addition is 5-30 weight parts to said copolymer of 100 weight parts. The examples of tackifier are, rosin ester, polyterpene resin, and hydrocarbon resin, and the like.

Skin-permeable active ingredient can be added into said composite in this invention. The examples are, anti-inflammatory drug such as ketoprofen and piroxicam, antihypertension, anesthetic, antibacterial, antifungal, vasodilator, antihistamine, cerebral circulation improvement, sex hormone such as estradiol, vitamins, whitening agent, moistening agent, and the like.

All drugs and cosmetic ingredients can be used in this invention so far as they can permeate into the skin. They can be dissolved or can be dispersed in said adhesive. When, the drug or cosmetic ingredient has hydroxyl group and/or carboxyl group, the crosslinking method should be careful from the viewpoint of stability of drug.

The preferred tape or sheet of the present invention has the construction of (flexible backing material/adhesive) or (flexible backing material/adhesive/release liner). In terms of adhesive strength of the tape to the skin, the tape that gives peeling force of 50-400 g/25 mm width to bakelite board is preferred.

Many manufacturing process of the tape of this invention may be adopted. For example, said copolymer, said softening agent, said crosslinking agent if needed, a drug or a cosmetic ingredient, etc., are mixed to obtain the coating solution. If needed, ethyl acetate, toluene, etc. are added to the solution for the viscosity adjustment. Thus obtained coating solution is coated onto release liner with a thickness of 0.01-0.2 mm (in terms of dry adhesive thickness). After removing the solvent by heating, the sheet is laminated onto flexible backing material.

As for the above-mentioned flexible backing material, plastic film such as polyethylene terephthalate and polypropylene, nonwoven fabric, paper, foam, and the like are used.

As for the above-mentioned release liner, The siliconized film or sheet selected from polyethylene terephthalate, polypropylene, paper, and the like are used.

BEST MODE FOR CARRYING OUT THE INVENTION

Then, examples of the present invention are described. Hereafter, "part" means "weight part" and "%" means "weight %."

Example 1

Under nitrogen atmosphere, olefinic macromonomer, KRATON LIQUID Polymer HPVM-1253 (Shell Chemical Company) of 40 parts, 2-ethylhexyl acrylate of 30 parts, N-vinyl-2-pyrrolidone of 20 parts, and 2-hydroxyethyl acrylate of 10 parts, were polymerized at 70° C. with azobisisobutironitrile of 0.05 parts as initiator in ethyl acetate of 200 parts, for 24 hours, and the copolymer solution was prepared.

To the copolymer solution of 100 parts (in terms of solid), 30 parts of isopropyl myristate was added, thus giving the coating solution. The viscous solution thus obtained was coated onto polyethylene terephthalate release liner of 75-micrometer thickness, the thickness of coating solution was adjusted to be adhesive layer of 80 micrometer (in terms of solid). The coated solution was dried for 20 minutes at 80° C., and the adhesive sheet was prepared. The polyethylene terephthalate film with thickness of 40 micrometer was laminated on this adhesive layer, and the skin tape was prepared.

The MWD of copolymer obtained by using GPC had two peaks. The molecular weight of the higher molecular peak was 427,000, and the molecular weight of lower molecular weight peak was 3,300.

The details of MWD measurement were as follows;

The copolymer solution was dried, and the obtained solid copolymer was dissolved into THF with a concentration of 3.0 mg/ml, as the sample solution. The apparatus used was LC-08, Japan Bunnseki Kogyo, with three columns connected in series, namely Shima-pack GPC806, 843, and 801, Shimadzu Seisakusyo, Japan. After filtration, the sample solution of 300 microliter was chromatographed. The eluent was THF with the flow rate of 1 ml/min. The ambient temperature was 40° C., and the refractive index detector was used. The chromatogram thus obtained was analyzed with the calibration curve obtained from polystyrene standards samples. The MWD was determined in terms of polystyrene. The same procedure was adopted for every example and comparative example.

Example 2

The same procedure as Example 1 was repeated to obtain the skin sheet, except that the amount of isopropyl myristate was changed to 50 parts.

Example 3

The same procedure as Example 1 was repeated to obtain the skin sheet, except that the amount of isopropyl myristate was changed to 70 parts.

Example 4

The same procedure as Example 1 was repeated to obtain the skin sheet, except that the amount of isopropyl palmitate of 100 parts instead of isopropyl myristate of 30 parts was used, and that tetrabutyl titanate of 2 parts was added as the crosslinker into the adhesive solution.

Example 5

The same procedure as Example 4 was repeated to obtain the skin sheet, except that the amount of isopropyl palmitate was changed to 150.

Example 6

The same procedure as Example 4 was repeated to obtain the skin sheet, except that the amount of isopropyl palmitate was changed to 200.

Comparative Example 1

Under nitrogen atmosphere, 2-ethylhexyl acrylate of 95 parts, acrylic acid of 5 parts were polymerized at 70° C. with azobisisobutironitrile of 0.05 parts as initiator in ethyl acetate of 200 parts for 24 hours, and the copolymer solution was prepared.

To the copolymer solution of 100 parts (in terms of solid), 15 parts of isopropyl myristate was added, thus giving the coating solution. The solution obtained was coated onto polyethylene terephthalate release liner of 75-micrometer thickness, the thickness of coating solution was adjusted to be adhesive layer of 80 micrometer (in terms of solid). The coated solution was dried for 20 minutes at 80° C., and the adhesive sheet was prepared. The polyethylene terephthalate film with thickness of 40 micrometer was laminated on this adhesive layer, and the skin tape was prepared.

The MWD of copolymer obtained by using GPC showed one peak. The molecular weight of peak was 327,000.

Comparative Example 2

The same procedure as Comparative example 1 was repeated to obtain the skin sheet, except that the amount of isopropyl myristate was changed to 50 parts.

Comparative Example 3

The same procedure as Comparative example 1 was repeated to obtain the skin sheet, except that the amount of isopropyl myristate was changed to 70 parts.

Comparative Example 4

The same procedure as Example 1 was repeated to obtain the skin sheet, except that the isopropyl palmitate of 100 parts was used instead of isopropyl myristate of 30 parts.

(Comparative Example 5

The same procedure as Comparative example 4 was repeated to obtain the skin sheet, except that the amount of isopropyl palmitate was 150 parts.

Comparative Example 6

The same procedure as Comparative example 4 was repeated to obtain the skin sheet; except that the amount of isopropyl palmitate was 300 parts, and that tetrabutyl titanate of 0.2 parts as the crosslinker was added.

Example 7

The same procedure as Example 1 was repeated to obtain the skin sheet, except that ethyl oleate of 50 parts instead of isopropyl myristate of 30 parts and rosin of 10 parts (tackifier) were added into the copolymer solution.

Comparative Example 7

The same procedure as Example 1 was repeated to obtain the skin sheet, except that the softener was removed.

Example 8

Under nitrogen atmosphere, olefin macromonomer, KRATON LIQUID Polymer HPVM-1253 (Shell Chemical Company) of 50 parts, butyl acrylate of 23 parts, methoxyethyl acrylate of 26 parts, and acrylic acid of 1 parts were polymerized at 70° C. with benzoyl peroxide of 0.02 parts as initiator in ethyl acetate of 100 parts for 24 hours, and the copolymer solution was prepared.

To the copolymer solution of 100 parts (in terms of solid), 50 parts of octyldodecyl lactate, and 8 parts of estradiol was added, thus giving the coating solution. The solution obtained was coated onto polyethylene terephthalate release liner of 75-micrometer thickness, the thickness of coating solution was adjusted to be adhesive layer of 80 micrometer (in terms of solid). The coated solution was dried for 20 minutes at 80° C., and the adhesive sheet was prepared. The polyethylene terephthalate film with thickness of 40 micrometer was laminated on this adhesive layer. After aging at 40° C. for 2 days, the skin tape was prepared.

The MWD of copolymer obtained by using GPC showed two peaks. The molecular weight of the higher molecular peak was 524,000, and the molecular weight of lower molecular weight peak was 4,300.

Example 9

The same procedure as Example 1 was repeated to obtain the skin sheet, except that the amount of isopropyl myristate was of 100 parts, and that tetrabutyl titanate of 0.2 parts was added, and that ketoprofen of 20 parts was added.

Example 10

Under nitrogen atmosphere, olefin macromonomer, KRATON LIQUID Polymer HPVM-1253 (Shell Chemical Company) of 50 parts, 2-ethylexyl acrylate of 30 parts, vinyl acetate of 18 parts, and acrylic acid of 2 parts were polymerized at 70° C. with benzoyl peroxide of 0.02 parts as initiator in ethyl acetate of 100 parts for 24 hours, and the copolymer solution was prepared. To the copolymer solution of 100 parts (in terms of solid), 50 parts of diisostearyl malate, and 5 parts of piroxicam was added, thus giving the coating solution. The following procedure was as the same as that of Example 8, and the skin tape was prepared.

The MWD of copolymer obtained by using GPC showed two peaks. The molecular weight of the higher molecular peak was 412,000, and the molecular weight of lower molecular weight peak was 4,200.

Example 11

The same procedure as Example 8 was repeated to obtain the skin sheet, except that cetyl isooctanoate of 100 parts instead of octyldodecyl lactate of 50 parts was added and that polyisocyanate, Koronate HL, Nippon Polyurethane, Japan, of 1 part was added.

Example 12

Under nitrogen atmosphere, olefin macromonomer, KRATON LIQUID Polymer HPVM-1253 (Shell Chemical Company) of 50 parts, dodecyl acrylate of 40 parts, stearyl acrylate of 4 parts, vinylpyrollidone of 15 parts, hydroxyethyl acrylate of 10 parts, and acrylic acid of 1 part were polymerized at 70° C. with benzoyl peroxide of 0.02 parts as initiator in ethyl acetate of 150 parts for 24 hours, and the copolymer solution was prepared.

To the copolymer solution of 100 parts (in terms of solid), 50 parts of tri-2-ehylhexanate and 4 parts of piroxicam were added, thus giving the coating solution. The following procedure was the same as that of Example 8 and the skin tape was prepared.

The MWD of copolymer obtained by using GPC showed two peaks. The molecular weight of the higher molecular peak was 472,000, and the molecular weight of lower molecular weight peak was 4,200.

Comparative Example 8

Styrene isoprene rubber, Craton 1107 (Craton polymer Japan), of 100 parts, hydrogenated rosin ester of 100 parts, liquid paraffin of 30 parts and ketoprofen of 4 parts, were dissolved in toluene of 500 parts, and the coating solution was obtained. After that, the same coating procedure as Comparative example 1 was adopted and the skin sheet was obtained.

Comparative Example 9

Under nitrogen atmosphere, olefin macromonomer, KRATON LIQUID Polymer HPVM-1253 (Shell Chemical Company) of 70 parts, 2-ethylhexyl acrylate of 10 parts, and N-vinyl-2-pirrolidone 20 parts were polymerized at 70° C. with azobisisobutyronitrile of 0.025 parts as initiator in ethyl acetate of 200 parts. At 5 hours after beginning of the polymerization, the gelation of polymer solution began and after 7 hours the polymerization was stopped because of severe gelation.

Comparative Example 10

Under nitrogen atmosphere, olefin macromonomer, KRATON LIQUID Polymer HPVM-1253 (Shell Chemical Company) of 15 parts, 2-ethylhexyl acrylate of 60 parts, n-vinyl-2-pyrollidone of 20 parts, and acrylic acid of 5 parts were polymerized at 70° C. for 24 hours with azobisisobutyronitrile of 0.025 parts as initiator in ethyl acetate of 200 parts, and the copolymer solution was prepared.

To the copolymer solution of 100 parts (in terms of solid), 15 parts of isopropylmyristate was added, thus giving the coating solution. The following procedure was the same as that of Example 1 and the skin tape was prepared.

The MWD of copolymer obtained by using GPC showed one peak. The molecular weight of the peak was 583,000.

Comparative Example 11

The same procedure as Comparative example 10 was repeated to obtain the skin sheet, except that the amount of isopropyl myristate was 50 parts.

Comparative Example 12

The same procedure as Comparative example 10 was repeated to obtain the skin sheet, except that the amount of isopropyl myristate was 70 parts.

Evaluation

The following examinations were performed after storing the above obtained samples for two weeks under 40° C. and 75% of humidity conditions.

(Adhesive Strength Examination)

The tape sample cut in width of 25 mm was stuck on the bakelite board. After pressing the tape twice with a roller of 300 g, the measurement of 180 degrees peel strength was carried out with the peeling speed of 300 mm/min. Thus obtained results are shown in Table 1.

(Paper Removal Test)

The tape sample cut in width of 25 mm was stuck on the newspaper. After pressing the tape twice with a roller of 300 g of load, the tape was peeled off with 300 mm/min speed. Both of the removal of paper (or paper torn away) by the adhesive and the cohesion failure of adhesive were examined. Thus obtained results are shown in Table 1.

TABLE 1

| Ex. No | Softening Agent (Amount, wt. Part) | Cross linker | Adhesion Strength (g/25 mm) | Paper Torn Away | Cohesion Failure |
|---|---|---|---|---|---|
| Ex. 1 | IPM (30) | − | 220 | Not observed | Not observed |
| Ex. 2 | IPM (50) | − | 190 | Not observed | Not observed |
| Ex. 3 | IPM (70) | − | 160 | Not observed | Not observed |
| Ex. 4 | IPP (100) | + | 230 | Not observed | Not observed |
| Ex. 5 | IPP (150) | + | 200 | Not observed | Not observed |
| Ex. 6 | IPP (200) | + | 190 | Not observed | Not observed |
| Ex. 7 | EO (50) | − | 250 | Not observed | Not observed |
| Ex. 8 | OL (50) | − | 170 | Not observed | Not observed |
| Ex. 9 | IPM (100) | + | 200 | Not observed | Not observed |
| Ex. 10 | SM (50) | − | 130 | Not observed | Not observed |
| Ex. 11 | SO (100) | + | 190 | Not observed | Not observed |
| Ex. 12 | GE (50) | − | 100 | Not observed | Not observed |
| Co. Ex. 1 | IPM (15) | − | 1350 | Observed | Not observed |
| Co. Ex. 2 | IPM (50) | − | * | # | Observed |
| Co. Ex. 3 | IPM (70) | − | * | # | Observed |
| Co. Ex. 4 | IPP (100) | − | * | # | Observed |
| Co. Ex. 5 | IPP (150) | − | * | # | Observed |
| Co. Ex. 6 | IPP (300) | + | 0 (✗) | Not observed | Not observed |
| Co. Ex. 7 | (0) | − | 890 | Observed | Not observed |
| Co. Ex. 8 | Rosin (30) | − | 1250 | Observed | Not observed |
| Co. Ex. 10 | IPM (15) | − | 1440 | Observed | Not observed |
| Co. Ex. 11 | IPM (50) | − | * | # | Observed |
| Co. Ex. 12 | IPM (70) | − | * | # | Observed |

Ex. (Example),
Co. Ex. (Comparative Example)
IPM (Isopropyl myristate),
IPP (Isopropyl palmitate),
EO (Ethyl oleate),
OL (Octyldodecyl lactate),
SM (Diisostealy malate),
SO (cetyl isooctanoate),
GE tri-2-ehylhexanate.
* Because of the cohesive failure, the determination could not be performed.
Major part of adhesive left on the paper.
✗ The bleeding of the IPP on the adhesive was severe.

The skin adhesives from Comparative examples 2-6 and 11-12 were too soft so that the adhesive showed the cohesion failure. When it was applied on the skin, a part of adhesive left on the skin after the removal. Hence these adhesives were unsuitable as skin adhesive, the subsequent skin irritation test was not carried out for these adhesives.

(Skin Irritation Study)

The sample tape with a diameter of 2.0 cm was applied to the inside of three volunteers' upper arm. It was removed after 24-hours, and the average value of skin irritation just after the removal was calculated according to the irritation index that shown below. The results are shown in Table 2.

<Irritation index >
0: No skin irritation,
1: Very slight irritation,
2: Slight irritation
3: Irritation
4: Severe irritation

TABLE 2

| Ex. No | Softening Agent (Amount, Wt. Part) | Skin Irritation |
|---|---|---|
| Ex. 1 | IPM (30) | 0.33 |
| Ex. 2 | IPM (50) | 0.33 |
| Ex. 3 | IPM (70) | 0.67 |
| Ex. 4 | IPP (100) | 0.33 |
| Ex. 5 | IPP (150) | 0.67 |
| Ex. 6 | IPP (200) | 0.33 |
| Ex. 7 | EO (50) | 0.67 |
| Ex. 8 | OL (50) | 0.67 |
| Ex. 9 | IPM (100) | 0.33 |
| Ex. 10 | SM (50) | 0.33 |
| Ex. 11 | SO (100) | 0.67 |
| Ex. 12 | GE (50) | 0.33 |
| Co. Ex. 1 | IPM (15) | 1.67 |
| Co. Ex. 7 | — (0) | 1.33 |
| Co. Ex. 8 | Liquid paraffin (30) | 2.00 |
| Co. Ex. 10 | IPM (15) | 2.00 |

(Drug Stability Test)

After storage of the sample tape, the drug content in tape samples were determined. Firstly, the theoretical drug content in a patch of 2.0 cm diameter was calculated by measuring the weight of the patch. Then, it was put into 50 cc ethanol for drug extraction at 36° C. for 24 hours. The drug content was determined with HPLC.

<HPLC Condition>
Detector: UV photometer (wavelength=230-280 nm)
Column: ODS type, inner diameter of 4-8 mm, length of 50-300 mm
Column temperature: 40° C.
Eluent:
For estradiol . . . Acetonitrile:water(55:45, volume ratio)
For ketoprofen . . . Acetonitrile:water(pH3.0)(60:40, volume ratio)
For piroxicam . . . Acetonitrile:water(pH3.0) (42:58, volume ratio)
The results are shown in Table 3.

TABLE 3

| Ex. No. | (Content-measured)/(Content-theoretical) |
|---|---|
| Ex. 8 | 0.96 |
| Ex. 9 | 0.94 |
| Ex. 10 | 0.98 |
| Ex. 11 | 0.98 |
| Ex. 12 | 0.97 |

Content-measured (Drug in patch determined with HPLC)
Content-theoretical (Drug in patch calculated)

Content-measured (Drug in patch determined with HPLC)
Content-theoretical (Drug in patch calculated)

The content of drug in all example tapes did not decrease during the storage time. This indicates that above adhesives are suitable for loading the drugs.

EFFECTS OF THE INVENTION

The present invention provides a pressure-sensitive adhesive is characterized by comprising (a) 100 parts by weight of a copolymer which is prepared from an olefinic macromonomer and a vinyl monomer and whose molecular weight has a two-peak distribution, and (b) 20 to 250 parts by weight of a softener which is compatible with the copolymer and liquid or pasty at room temperature and has a boiling point of 250 or above (with the proviso that when the content of the softener (b) exceeds 80 parts by weight, the copolymer must be post-cured). The tape or sheet for the skin made from the above adhesive is re-peelable and does not give damage to the skin. Therefore, the tape or sheet of this invention is quite useful for dressing tape, medicated tape, and cosmetic sheet.

The invention claimed is:

1. A transdermal pressure-sensitive adhesive comprising:
   (a) 100 parts by weight of a copolymer prepared by a process of solution polymerization involving simultaneous polymerization of four monomers including an olefinic macromonomer selected from the group consisting of polyethylene, polypropylene, ethylene-propylene copolymer, and ethylene-butylene copolymer, alkyl (meth)acrylate, at least one first vinyl monomer selected from the group consisting of n-vinyl-2-pyrrolidone, vinyl acetate and alkoxyalkyl (meth) acrylate, and a second vinyl monomer having a functional group selected from the group consisting of hydroxyl group, carboxyl group, glycidyl group, and amino group, said copolymer consisting of:
   20 to 65% by weight of said olefinic macromonomer,
   20 to 40% by weight of said alkyl (meth)acrylate,
   10 to 40% by weight of said first vinyl monomer
   and 0.5 to 25% by weight of said second vinyl monomer,
      thereby forming a random copolymer from these monomers, said copolymer having a molecular weight (in terms of polystyrene and as determined by gel permeation chromatography (GPC)) with a two-peak distribution (with the proviso that when the copolymer is to be post-cured, the distribution is one as determined before the post cure), and
   (b) 20 to 250 parts by weight of a softener which is compatible with the copolymer and liquid or pasty at room temperature and has a boiling point of 250° C. or above (with the proviso that when the content of the softener (b) exceeds 80 parts by weight, the copolymer must be post-cured).

2. A transdermal pressure-sensitive adhesive composition comprising:
   (1) a pressure-sensitive adhesive comprising;
   (a) 100 parts by weight of a copolymer which is prepared by a process of solution polymerization involving simultaneous polymerization of four monomers including an olefinic macromonomer selected from the group consisting of polyethylene, polypropylene, ethyl-propylene copolymer, and ethylene-butylene copolymer, alkyl (meth)acrylate, at least one first vinyl monomer selected from the group consisting of n-vinyl-2-pyrrolidone, vinyl acetate and alkoxyalkyl (meth)acrylate, and a second vinyl monomer having a functional group selected from the group consisting of hydroxyl group, carboxyl group, glycidyl group, and amino group, said copolymer consisting of:
   20 to 65% by weight of said olefinic macromonomer,
   20 to 40% by weight of said alkyl (meth)acrylate,
   10 to 40% by weight of said first vinyl monomer
   and 0.5 to 25% by weight of said second vinyl monomer,
      thereby forming a random copolymer from these monomers, said copolymer having a molecular weight (in terms of polystyrene and as determined by gel permeation chromatography (GPC)) with a two-peak distribution (with the proviso that when the copolymer is to be post-cured, the distribution is one as determined before the post cure), wherein a higher molecular weight peak is within 200,000 to 800,000, while a lower molecular weight peak is within 2,000 to 7,000; and
   (b) 20 to 250 parts by weight of one or more kinds of softeners selected from the group consisting of isopropyl myristate, isopropyl palmitate, ethyl oleate, octyldodecyl myristate, cetyl isooctanoate, octyldodecyl oleate, glyceryl tri-2-ethylhexanate, neopentyl glycol, diethyihexanoate, octyldodecyl lactate, and diisostearyl malate (with the proviso that when the content of the softener (b) exceeds 80 parts by weight, the copolymer must be post-cured); and
   (2) one or more of a drug or cosmetic active ingredient being dissolved or dispersed in said pressure-sensitive adhesive.

3. The transdermal pressure-sensitive adhesive according to claim 1, wherein said softener is selected from the group consisting of isopropyl myristate, isopropyl palmitate, ethyl oleate, octyldodecyl myristate, cetyl isooctanoate, octyldodecyl oleate, glyceryl tri-2-ethylhexanate, neopentyl glycol, diethyihexanoate, octyldodecyl lactate, and diisostearyl malate.

4. The transdermal pressure-sensitive adhesive according to claim 1, wherein 5 to 30 weight parts of tackifier is added to 100 weight parts of said copolymer (a).

5. A tape or sheet for the skin wherein said pressure-sensitive adhesive according to claim 1, is laid on at least one surface of a backing material.

6. A tape or sheet for the skin, comprising said transdermal pressure-sensitive adhesive according to claim 1, and further comprising a skin-permeable active ingredient,
   wherein said transdermal pressure-sensitive adhesive is laid on at least one surface of a backing material.

7. The tape or sheet for skin according to claim 6, wherein said skin-permeable active ingredient is a drug or a cosmetic ingredient.

* * * * *